United States Patent
Schoemaker

(10) Patent No.: US 7,041,303 B2
(45) Date of Patent: May 9, 2006

(54) USE OF MOXONIDINE FOR POSTMYOCARDIAL INFARCTION TREATMENT

(75) Inventor: Regina Geertruida Schoemaker, Rotterdam (NL)

(73) Assignee: Solvay Pharmaceuticals GmbH, Hannover (DE)

( * ) Notice: Subject to any disclaimer, the term of this patent is extended or adjusted under 35 U.S.C. 154(b) by 0 days.

(21) Appl. No.: 09/917,858

(22) Filed: Jul. 31, 2001

(65) Prior Publication Data

US 2002/0045633 A1    Apr. 18, 2002

Related U.S. Application Data

(63) Continuation of application No. PCT/EP00/00655, filed on Jan. 28, 2000.

(30) Foreign Application Priority Data

Feb. 1, 1999  (DE) ................... 199 03 780

(51) Int. Cl.
    *A61K 9/00* (2006.01)
(52) U.S. Cl. ............. 424/400; 424/422; 424/464; 514/821; 514/256; 514/269; 514/393; 514/398; 514/399
(58) Field of Classification Search ........... 514/256, 514/269, 397, 398, 399, 821; 424/400, 422, 424/464
    See application file for complete search history.

(56) References Cited

FOREIGN PATENT DOCUMENTS

| EP | 0317855 | 8/1990 |
|---|---|---|
| WO | WO9746241 | 12/1997 |

OTHER PUBLICATIONS

Howes et al. Comparative effects of angiotensin converting enzyme inhibition (perindopril) or diuretic therapy on cardiac hypertrophy and sympathetic activity following myocardial infarction in rats. Cardiovascular Drug Therapy, Feb., 1991, 5(1):147-152.*

Rene Roland Wenzel, "$I_1$-Imidazoline Agonist Moxonidine Decrease Sympathetic Nerve Activity and Blood Pressure in Hypertensives" Hypertension, Dec. 1998.

W. Lada, "Imidazoline-prefering receptors and the $I_1$-imidazoline blocking therapy" Pol. Merk. Lek., 1996.

Istvan Lepran, "Effect of Moxonidine on Arrhythmias Induced by Coronary Artery Occlusion and Reperfusion" Journal of Cardiovascular Pharmacology, 1994.

* cited by examiner

Primary Examiner—Thurman K. Page
Assistant Examiner—Lakshmi Channavajjala
(74) Attorney, Agent, or Firm—Crowell & Moring LLP

(57) ABSTRACT

A method of treating myocardial damage secondary to myocardial infarction using moxonidine or a physiologically compatible salt thereof. Pharmaceutical preparations containing moxonidine and its physiologically compatible acid addition salts are suitable for use in acute myocardial infarction and/or postmyocardial infarction management. In addition to a beneficial influence, promoting recovery and/or rehabilitation, on the myocardial status following myocardial infarction, moxonidine and its physiologically compatible acid addition salts, especially when used in the management of postmyocardial infarction patients in the chronic stage, also show a preventive effect against the progression of heart failure after myocardial infarction.

5 Claims, No Drawings

USE OF MOXONIDINE FOR POSTMYOCARDIAL INFARCTION TREATMENT

CROSS REFERENCE TO RELATED APPLICATIONS

This application is a continuation of international patent application no. PCT/EP00/00655, filed Jan. 28, 2000, designating the United States of America, the entire disclosure of which is incorporated herein by reference. Convention priority is claimed based on Federal Republic of Germany patent application no. DE 199 03 780.9, filed Feb. 1, 1999.

BACKGROUND OF THE INVENTION

The present invention relates to the use of 4-chloro-5-[(4,5-dihydro-1H-imidazol-2-yl)-amino]-6-methoxy-2-methylpyrimidine (=moxonidine) and its physiologically compatible acid addition salts for the treatment of myocardial damage secondary to myocardial infarction and for the production of pharmaceutical preparations suitable for this treatment.

SUMMARY OF THE INVENTION

The object of the invention is to provide new pharmaceutical preparations that exert a beneficial influence, promoting recovery and/or rehabilitation, on the myocardial status of myocardial infarction patients and which are therefore suitable for the treatment of myocardial damage secondary to myocardial infarction within the context of myocardial infarction and/or postmyocardial infarction management.

According to the invention, 4-chloro-5-[(4,5-dihydro-1H-imidazol-2-yl)-amino]-6-methoxy-2-methylpyrimidine of Formula I

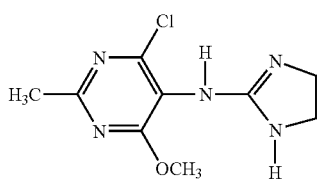

and its physiologically compatible acid addition salts are used for the manufacture of pharmaceutical preparations for the treatment of myocardial damage secondary to myocardial infarction.

Suitable physiologically compatible acid addition salts of moxonidine include salts with inorganic acids, for example hydrohalic acid, or with organic acids, for example low molecular weight aliphatic mono- or dicarboxylic acids such as acetic acid, fumaric acid or tartaric acid or aromatic carboxylic acids such as e.g. salicylic acid.

The compounds used according to the invention fall within the scope of the 5-[(2-imidazolin-2-yl)-amino]-pyrimidine derivatives with blood pressure lowering properties described in German Patent Application No. 28 49 537, and are known from this patent application. Pharmaceutical preparations containing moxonidine are commercially available as antihypertensive medications under the trade name Physiotens® and are used medically as antihypertensive agents. The compounds can be manufactured in a manner known in the art according to the process described in the aforementioned patent application or in a manner analogous to these processes.

It has now surprisingly been found that moxonidine and its physiologically compatible acid addition salts exert a beneficial effect, promoting recovery and/or rehabilitation, on the myocardial status following myocardial infarction and are therefore suitable for the treatment of myocardial damage secondary to myocardial infarction in man and larger mammals.

A myocardial infarction is generally understood to mean necrosis of a circumscribed area of heart muscle due to persisting complete interruption or critical reduction of blood supply to this area. In addition to general therapeutic measures (analgesia and sedation, oxygen administration, bed rest and diet) the management of acute myocardial infarction comprises especially thrombolytic or fibrinolytic therapy with the aim of preserving as much (primary) ischemic myocardium as possible from final cell death (e.g. definitive necrosis) by reperfusing the ischemic area and thereby restricting the infarct size to the smallest possible area. Further (supportive) measures can contribute to improving myocardial status, especially in the region of the infarct area, both in the acute phase of myocardial infarction and in the postmyocardial infarction phase.

The compounds used according to the invention for the treatment of myocardial damage secondary to myocardial infarction are suitable for general use in the management of myocardial infarction. They can therefore already be used for the treatment of acute myocardial infarction and especially for postmyocardial infarction management both in patients who have already received fibrinolytic treatment and in patients without such lysis. In postinfarction patients with lysis, treatment with the compounds used according to the invention in particular also has the effect of preventing the development of cardiac insufficiency of myocardial origin (myocardial heart failure). This also applies to such patients who have already been treated with b-adrenoceptor blocking drugs.

Postinfarction patients who have not undergone lysis pass into the chronic phase of myocardial infarction. For postinfarction patients in the chronic stage, the important role played by the sympathetic nervous system (SNS) in cardiovascular regulation is of particular significance. For example, sympathetic stimulation is the primary mechanism for increasing cardiac output, since this stimulation causes both an increase in myocardial contractility and heart rate. Acute myocardial infarction results, among other things, in activation of the SNS to maintain perfusion pressure and tissue perfusion. This acute situation can develop into a more chronic phase in which the sympathetic activation contributes to hypertrophy and remodelling processes in the non-infarcted myocardium. This process, however, can progress beyond the desired degree and the continued SNS activation may become harmful for various reasons:

1) Chronic activation of the central sympathetic nervous system is to be regarded as unfavorable as regards the progression of heart failure. Persisting adrenergic stimulation results in a compensatory reduction of adrenergic receptors in the heart. The consequence of this protective mechanism of the heart against persistently elevated catecholamine levels, however, is significant impairment of the regulation of heart rate and the force of myocardial contraction via the autonomic nervous system.
2) The SNS stimulation increases vascular tone and consequently the after load of the heart.

3) Increased circulating catecholamine levels induce focal necrosis in the heart and contribute to the development of cardiac hypertrophy.
4) Elevated plasma catecholamine levels contribute to the unfavorable increase of the heart rate and to the development of sometimes life-threatening cardiac arrhythmias.

The prevention and abolition of excessive sympathetic activation can therefore represent a desirable strategy for the management of myocardial infarction patients, especially also with the aim of preventing the progression of heart failure after myocardial infarction.

It has now surprisingly been found that moxonidine used according to the invention for myocardial infarction and/or postmyocardial infarction management is distinguished by a surprising beneficial influence, promoting recovery and/or rehabilitation, on the functional status of the myocardium of myocardial infarction patients, especially of postmyocardial infarction patients in the chronic stage. Administration of moxonidine after myocardial infarction causes a reduction of cardiac weight and a reduction of sympathetic activation, as demonstrated by measurement of plasma noradrenaline levels. Moxonidine is therefore suitable for the reduction of excessive cardiac hypertrophy, especially in later phases of postmyocardial infarction treatment. Furthermore, moxonidine decreases plasma noradrenaline levels, allowing sympathetic activation after myocardial infarction to be effectively normalized.

For the treatment of myocardial damage secondary to myocardial infarction according to the invention, moxonidine and its physiologically compatible acid addition salts can be administered orally, intravenously or transdermally in conventional pharmaceutical preparations.

Thus, moxonidine and its physiologically compatible acid addition salts may be included, in an amount effective in promoting recovery and/or rehabilitation of myocardial status, with conventional pharmaceutical excipients and/or vehicles in solid or liquid pharmaceutical preparations. Examples of solid formulations, which can be formulated for immediate or sustained release of the drug, are preparations suitable for oral administration such as tablets, coated tablets, capsules, powders or granules, but also suppositories. These solid preparations may contain conventional pharmaceutical inorganic and/or organic vehicles such as lactose, talc or starch as well as conventional pharmaceutical excipients such as lubricants or tablet disintegrants. In case of patches the drug is placed in a drug reservoir, in particular e.g. in a drug matrix (e.g. a polymeric matrix). Liquid preparations such as solutions, suspensions or emulsions of the active ingredients can contain the usual diluents such as water, oils and/or suspending agents such as polyethylene glycols and the like. Further excipients may also be added, such as preservatives, flavoring agents and the like.

The active ingredients can be mixed and formulated with the pharmaceutical adjuvants and/or carriers in a manner known in the art. To manufacture solid dosage forms, the active ingredients may for example be mixed with the excipients and/or vehicles in the usual manner and wet or dry granulated. The granules or powder can be filled directly into capsules or compressed into tablet cores in the usual manner. If desired, these cores can be coated in the manner known to the art. Patches or transdermal therapeutic systems can be constructed in the conventional manner, e.g. of cover layer, drug reservoir (self-adhesive or with additional adhesive layer) and stripp-off layer, as matrix controlled systems as well as membrane controlled systems (e.g. equipped with additional control membrane).

Tests and Test Results

The beneficial actions of moxonidine in the management of myocardial infarction and especially postmyocardial infarction can be demonstrated in standard tests for the determination of pharmacological indicators of the effect of substances on factors that influence the functional status of the myocardium after myocardial infarction. A suitable animal model for demonstrating effects on factors that influence the functional status of the myocardium especially in the chronic stage of myocardial infarction are, for example, Wistar rats with chronic myocardial infarction (MI).

In this animal model (MI rats) it was found that plasma noradrenaline levels increase acutely after myocardial infarction. In the advanced stages of heart failure the plasma noradrenaline level can increase further. Close observation of the MI rats revealed that even three weeks after the infarction, i.e. after the "healing period", heart rate (measured in vivo on unconfined, conscious rats) appeared to be elevated, while the remaining plasma noradrenaline level was still about 50% higher than in sham rats (see below: sham-operated rats without ligation of the coronary artery). The central nervous system of these animals was also found to have increased metabolic activity in the paraventricular hypothalamus and the locus coeruleus, in which the sympathetic effects on the peripheral vessels are regulated. Behavioral studies showed increased anxiety levels in infarct rats. These observations therefore show that chronically elevated sympathetic activation was present in this rat infarct model.

Experimental Animals and Dosing:

The following studies were performed on male Wistar rats (270 to 320 g, Harlan Zeist, Netherlands). The rats were kept in rooms with a 12 h light/dark cycle and had free access to standard rat diet and water. The animals underwent coronary artery ligation (MI rats) or sham operation without ligation (sham rats). After 24 hours the MI rats were randomized and implanted with osmotic minipumps (Alzet, Model 2001) in order to administer moxonidine in a dose of 3 or 6 mg/kg-day s.c. (subcutaneously) or only operated on without pump implant. The moxonidine treatment was continued up to the end of the experiment three weeks after the surgical procedure.

Coronary Artery Ligation

The left anterior descending coronary artery was ligated under pentobarbital anesthesia (60 mg/kg, i.p.). Brief description: after intubation of the trachea, an incision was made in the skin over the $4^{th}$ intercostal space. The overlaying muscles were separated and kept aside. The animals were then placed on positive pressure ventilation (rate 65 to 70/min, stroke volume 3 ml) and the thoracic cavity was opened by cutting the intercostal muscles. The pericardium was opened. The heart was left in situ and a 6-0 silk suture was placed below the left coronary artery in the vicinity of the origin of the pulmonary artery. The suture was tightened. Sham rats were subjected to the same procedure but without actual ligation. The ribs were pulled together with 3-0 silk suture. The muscles were then returned to their original position and the skin was sutured.

Preparation and Collection of Blood Samples 19 days after the surgical procedure for coronary artery ligation the rats were again anesthetized with pentobarbital and a catheter (PE-10, heat-sealed with PE-50) was introduced through the femoral artery and placed in the abdominal aorta. The catheter was advanced subcutaneously as far as the animals' neck, where it was allowed to exit and was fixed and closed at the exit site. The rats were allowed a 2-day recovery period. On the day of sampling the catheter was lengthened with a heparin-treated, saline-filled tube and two 1-ml blood samples were collected after at least 60 minutes. Blood was collected in pre-cooled sample pots (syringes) prepared with 10 µl EDTA (0.1M). After centrifugation the plasma was collected in pre-cooled tubes containing either 1.2 mg glutathione or 10 µl aprotinin (100 KIU; KIU=kilo international units) in order to determine either catecholamines or atrial natriuretic factor (ANF). The tubes were stored at −80° C. The plasma concentrations of noradrenaline, adrenaline and dopamine were determined by HPLC, whereas the concentrations of ANF were analyzed using an RIA test.

Measurement of Cardiac Collagen

The quantity of interstitial collagen was determined on 6 to 7 hearts randomly selected from each experimental group. For this purpose the hearts were fixed by perfusion with 3.6% by weight phosphate buffered formaldehyde. After removal of the atria and large vessels, the ventricles were cut into four slices from the apex to the base of the heart and the slices were kept for at least 24 hours in formaldehyde. After fixation the slices were dehydrated and embedded in paraffin. Deparaffinized 5 µm sections were incubated for 5 min with 0.2% by weight/vol aqueous phosphomolybdic acid, and then for 45 min with 0.1% by weight Sirius red F3BA (Polysciences Inc., Northampton, UK) in saturated picric acid, then washed for 2 min with 0.01 M hydrochloric acid, dehydrated and embedded in Entellan (Merck, Darmstadt, Germany) for microscopic analysis. Interstitial collagen was determined, distant from the infarct site, in the interventricular septum of each heart as a Sirius red positive area at 40-fold magnification.

Data Analysis

The data obtained were expressed as group means ± SEM (standard error of the mean) unless otherwise stated. Only data of infarcted hearts with an infarct area covering the major portion of the free heart wall of the left ventricle were included in the evaluation since smaller infarct areas are usually fully compensated hemodynamically. The data were analyzed by one-way analysis of variance (ANOVA) followed by post-hoc Bonferroni analysis. Differences in the structural parameters in moxonidine treated and untreated infarcted hearts were determined by Student t-test independently for the two groups.

Results

Four groups of rats were studied: 2 moxonidine-treated infarct rats (dosage 3 and 6 mg/kg·day), untreated infarct rats and sham-operated control rats (SHAM rats). Coronary artery ligation produced a main infarction in the free wall of the left ventricle. Total mortality of the experimental animals was 29% and was the same in both infarct groups. Data of five rats of the 6 mg/kg·day group had to be excluded since their infarct area was too small. The results of the tests are summarized in Table 1 for experiments with a dosage of 6 mg/kg·day and for a dosage of 3 mg/kg·day, and are explained in the following. The results shown in Table 1 comprise the data of groups of 7 to 14 rats with the exception of the collagen measurements, for which the data refer to groups of 6 to 7 rats.

Although the body weight of the animals was similar at the beginning of the tests, moxonidine-treated infarct rats had a slightly lower body weight than the untreated infarct rats, but a significantly lower body weight than the sham rats. The cardiac weight of the moxonidine treated infarct rats was significantly lower than the cardiac weight of untreated infarct rats. These effects were dosage depending in the range from 3 to 6 mg/kg·day (see Table 1). It can be concluded from the data that excessive cardiac hypertrophy was prevented by moxonidine administration.

Neurohumoral activity measured based on plasma noradrenaline and ANF levels was significantly elevated in untreated infarct rats. Plasma ANF levels of rats treated with moxonidine were unchanged compared to those of untreated infarct rats. Plasma noradrenaline levels were reduced by moxonidine treatment to about half the value found for the sham rats.

The measured plasma noradrenaline levels were significantly increased in untreated infarct rats, reaching up to threefold the value of the sham rats. Plasma noradrenaline levels were reduced by treating infarct rats with moxonidine in the 6 mg/kg·day group to almost half the values of the sham rats. In the 3 mg/kg·day group the plasma noradrenaline levels were clearly reduced. This shows that the dose of 3 or 6 mg moxonidine/kg daily can effectively reduce sympathetic activation after myocardial infarction in rats.

The results of the measurement of the cardiac collagen are likewise evident from Table 1 for the 3 and 6 mg/kg·day groups.

Heart rate measured in conscious animals was markedly increased in infarct rats compared to sham rats. This tachycardia was not only prevented by moxonidine administration, the treated infarct rats even showed a slowing of cardiac activity (bradycardia) compared to the sham rats.

TABLE 1

Test results for sham-operated controls (SHAM), untreated infarct rats (INFARCT) and moxonidine-treated infarct rats (INF + MOX); dose 3 mg/kg daily and dose 6 mg/kg daily

|  | SHAM | INFARCT | INF + MOX (3 mg) | INF + MOX (6 mg) |
|---|---|---|---|---|
| Number of animals | 8 – 14 | 7 – 12 | 7 | 6 – 7 |
| Body weight (g) | 333 ± 7 | 320 ± 10 | 301 ± 5 | 299 ± 9* |
| Heart weight (mg) | 1174 ± 37 | 1543 ± 75* | 1408 ± 104 | 1076 ± 24# |
| Heart/Body weight ratio | 3.5 ± 0.1 | 4.7 ± 0.3* | 4.7 ± 0.4* | 3.6 ± 0,2# |
| Heart rate (beats/min) | 351 ± 17 | 387 ± 8* | 334 ± 12# | 321 ± 6*# |
| MAP (mmHg) | 111 ± 2 | 98 ± 3* | 87 ± 3* | 100 ± 5 |
| Plasma NA level (pg/ml) | 199 ± 30 | 578 ± 143* | 345 ± 108 | 96 ± 20# |
| Plasma ANF (pg/ml) | 38 ± 3 | 53 ± 5 | (54 ± 2, n-3) | 61 ± 8 |
| Interstitial Collagen (%) | 1.3 ± 0.1 | 2.2 ± 0.3* | 2.4 ± 0.2* | 1.4 ± 0.1 |

Abbreviations:
MAP = mean arterial pressure; NA = noradrenaline;
ANF = atrial natriuretic factor
* = significantly different from sham rats
# = significantly different from untreated infarct rats These experimental results clearly suggest that the functional status of the myocardium can be beneficially influenced by the administration of moxonidine in the context of myocardial infarction treatment and especially postmyocardial infarction treatment. From the measured plasma catecholamine levels it can be concluded that moxonidine can effectively normalize sympathetic activation in infarct rats.

This result is confirmed by the heart rate data (in vivo, on conscious rats) since heart rate in moxonidine treated rats was even below the levels found for sham rats. This is presumably due more to a chronic than an acute effect of moxonidine, since in acute treatment the reduced heart rate is accompanied by a rise in mean arterial blood pressure not observed during chronic treatment. As regards the effect of moxonidine on cardiac remodelling, the results obtained are complex. Although the positive effects observed on the cardiac weight/body weight ratio (hypertrophy) appear not to be significant and the measurement of interstitial collagen suggests at most a minor remodelling effect, these results do reveal a recognizable trend towards a preventive effect of moxonidine against excessive cardiac hypertrophy and undesired remodelling.

The above experimental results therefore show that moxonidine and its acid addition salts exert a beneficial influence, promoting recovery and/or rehabilitation, on myocardial status after myocardial infarction and are therefore suitable for the treatment of myocardial damage secondary to myocardial infarction in humans and larger mammals, both in the management of acute myocardial infarction and especially also postmyocardial infarction management. Particularly in postmyocardial infarction management, moxonidine can also have a preventive effect on the progression of heart failure after myocardial infarction. The dosages of moxonidine or its acid addition salts to be administered may differ between individuals and naturally vary depending on the type of condition to be treated and the dosage form. The daily dosages for myocardial infarction and postmyocardial infarction management in man are generally 0.05 to 5 mg, preferably about 0.25 to 3.0 mg on oral administration. Moxonidine or its acid addition salts can be administered in pharmaceutical preparations designed for immediate, prolonged, controlled and/or regulated drug release. In this context it goes without saying for those skilled in the art that preparations for prolonged, controlled and/or regulated drug release may contain higher amounts of drug than preparations for immediate drug release.

The following example is provided to illustrate the manufacture of a pharmaceutical preparation containing moxonidine suitable for myocardial infarction and/or postmyocardial infarction treatment, without however restricting the scope of the application.

EXAMPLE 1

Moxonidine-containing film-coated tablets

| Composition: | |
|---|---|
| Tablet Cores: | |
| Moxonidine | 0.025 parts |
| Lactose | 9.575 parts |
| Povidone USP | 0.070 parts |
| Crospovidone USP | 0.300 parts |
| Magnesium stearate | 0.030 parts |
| (Water | 0.750 parts) |
| Total solids | 10.000 parts |
| Film coating: | |
| Hydroxypropylmethylcellulose | 0.156 parts |
| 30% aqueous ethylcellulose dispersion | 0.480 parts |
| (= solid) | (0.144) parts |

| Composition: | |
|---|---|
| Polyethylene glycol 6000 | 0.030 parts |
| Titanium dioxide | 0.150 parts |
| Talc | 0.1197 parts |
| Red iron oxide | 0.0003 parts |
| (Water | 3.864 parts) |
| Total solids | 0.600 parts |
| Total film-coating suspension | 4.800 parts |

In order to coat 10,000 tablet cores weighing 100 mg each, 4.8 kg of the above film coating suspension is used.

Production of Tablet Cores

The moxonidine and lactose were mixed. The mixture was thoroughly moistened with a solution of the binder povidone in water, thoroughly kneaded and the resulting product was spread out on trays and dried at a temperature of about 50° C. to a moisture content of not more than 0.5%. The dried product was passed through a 0.75 mm sieve (Frewitt machine). After mixing the resulting granules with crospovidone and magnesium stearate, cores with an individual weight of 100 mg were compressed such that each core contained 0.25 mg active ingredient.

Preparation of Film-Coating Suspension

The hydroxypropylmethylcellulose and the polyethylene glycol 6000 were dissolved in part of the water. A suspension of talc, titanium dioxide and iron oxide in the remaining water was added to this solution whilst stirring. The resulting suspension was diluted with the 30% aqueous ethylcellulose dispersion with gentle stirring.

Film Coating of Cores

The film coating suspension was sprayed onto the cores in a film coating apparatus while warm air at about 70° C. heated the cores to a temperature of about 45° C. The film-coated tablets were then dried for 16 hours at a temperature of about 45° C.

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

What is claimed is:

1. A method of treating myocardial damage secondary to myocardial infarction in a patient who has suffered a myocardial infarction, said method comprising administering to said patient who has suffered the myocardial infarction an amount of 4-chloro-5-[(4,5-dihydro-1H-imidazol-2-yl)-amino]-6-methoxy-2-methylpyrimidine corresponding to formula I:

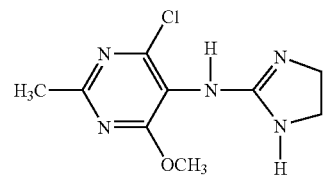

or a physiologically compatible salt thereof effective to inhibit myocardial damage secondary to myocardial infarction.

2. A method according to claim 1, wherein the compound of Formula I or physiologically compatible salt thereof is administered for treating myocardial damage secondary to myocardial infarction in acute myocardial infarction.

3. A method according to claim 1, wherein the compound of Formula I or physiologically compatible salt thereof is administered for postmyocardial infarction management.

4. A method according to claim 3, wherein the compound of Formula I or physiologically compatible salt thereof is administered for treating myocardial damage secondary to myocardial infarction in the management of chronic post-myocardial infarction patients.

5. A method according to claim 1, for treating myocardial damage secondary to myocardial infarction, wherein an amount of the compound of Formula I or physiologically compatible salt thereof that is effective in promoting recovery or rehabilitation of myocardial status is administered in admixture with at least one pharmaceutical adjuvant or carrier.

* * * * *